United States Patent [19]

Bouyssi et al.

[11] Patent Number: 4,809,690
[45] Date of Patent: Mar. 7, 1989

[54] PROTECTIVE SKULL CAP FOR THE SKULL

[75] Inventors: Jean-Francois Bouyssi; Thierry Massard, both of Paris; Jean Vienney, Lardy, all of France

[73] Assignee: Commissariat a l'Energie Atomique, Paris, France

[21] Appl. No.: 889,326

[22] Filed: Jul. 23, 1986

[30] Foreign Application Priority Data

Jul. 24, 1985 [FR] France .................. 85 11322

[51] Int. Cl.$^4$ .................. A61F 13/00; A61F 15/00
[52] U.S. Cl. .................. 128/157; 128/163; 128/76 R; 128/857; 2/195; 2/2; 2/410; 2/412; 428/137; 428/246; 428/286; 428/902
[58] Field of Search .................. D2/256; 2/6, 181.6, 2/412, DIG. 7, 410, 411, 195; 128/157, 163, 76 R, 132; 623/15; 428/137, 246, 286, 902; 264/257, 258, 308

[56] References Cited

U.S. PATENT DOCUMENTS

| | | | |
|---|---|---|---|
| 3,286,275 | 11/1966 | Marchello | 2/411 |
| 3,320,619 | 5/1967 | Lastnik et al. | 2/6 |
| 3,437,631 | 4/1969 | Cleveland | 2/410 |
| 3,691,000 | 9/1972 | Kalnin | 273/DIG. 23 |
| 3,833,935 | 9/1974 | Ansite et al. | 2/6 |
| 3,850,785 | 11/1974 | McQuade et al. | 428/902 |
| 3,956,447 | 5/1976 | Denommee et al. | 2/6 |
| 4,288,268 | 9/1981 | Hartung | 2/412 |
| 4,539,253 | 9/1985 | Hirschbuehler et al. | 273/DIG. 23 |
| 4,602,385 | 7/1986 | Warren | 2/410 |
| 4,614,684 | 9/1986 | Ebneth et al. | 264/258 |

FOREIGN PATENT DOCUMENTS 2335169  7/1977  France.
322226   6/1957  Switzerland.
9114     of 1914 United Kingdom.

OTHER PUBLICATIONS

Certified English Translation of French Patent No. 2,335,169 to Gallet Published Jul. 1977.

Primary Examiner—Richard J. Apley
Assistant Examiner—Paul Prebilic
Attorney, Agent, or Firm—Michael N. Meller

[57] ABSTRACT

An impression is firstly taken of the skull, which makes it possible to produce a replica thereof. On the latter are successively deposited a thermostable film, a first carbon fabric layer, a second aramide layer and a third carbon fabric layer. These three layers form the protective skull cap following polymerization in an oven and elimination of the skull replica and the thermostable film. The skull cap can optionally contain holes. A protective skull cap for at least partly covering a skull, where the cap is worn directly on the skin and is flexible to perfectly adapt to the shape of the skull so as to be in intimate contact therewith at all points. The skull cap consists of three layers, from the inside to the outside, a first carbon fabric layer, a second [ARAMIDE] polyarylamide fiber fabric layer and a third carbon fabric layer. These layers are impregnated with a high elongation resin so that the thickness of the cap is equal to or less than 1 mm.

4 Claims, 2 Drawing Sheets

PROTECTIVE SKULL CAP FOR THE SKULL

BACKGROUND OF THE INVENTION

The present invention relates to protection for the cerebral cortex and more particularly relates to a lighter and more pleasantly wearable protection than provided by the prior art.

Certain people have defects of the skull or cranium, either as a result of congenital deformity, or as a result of a serious traumatism. The cerebral cortex is then no longer naturally protected by the cranium bones. Generally, such people have to wear a motor cycle type helmet, which gives a complete protection, or a leather cyclist's helmet, which only provides minimum protection. In all cases, it is a relatively heavy and conspicuous object. The patient has to permanently wear this helmet, which closes many sporting and even social activities to him. In particular, with children or adolescents, the very conspicuous nature of the protection does not assist a normal development of the personality (invalid complex).

SUMMARY OF THE INVENTION

The object of the present invention is to eliminate these disadvantages by proposing a protective skull cap for the cranium or skull, which is lighter and easier to wear than the presently used helmets.

According to the main feature of the protective skull cap according to the invention, the latter is intended to at least partly cover a skull and from the inside to the outside, said skull cap comprises a first carbon fabric layer, a second ARAMIDE fiber fabric layer and a third carbon fabric layer.

Preferably, at least one of these layers and if possible all three is impregnated with a resin, which is preferably a high elongation resin. There can also be a plurality of holes, each of which passes through the three layers of the skull cap.

According to another feature of the invention, the thickness of the skull cap is less than 1 mm and preferaly less than 0.5 mm, said thickness generally being between 0.3 and 0.5 mm.

The invention also relates to a process for producing a protective skull cap for the skull. According to the main feature of this process, it comprises the following stages consisting of:

(a) producing a replica of the skull, (b) successively depositing on the skull replica a first carbon fabric layer, a second ARAMIDE fiber layer and a third carbon fabric layer, (c) subjecting the entity to a polymerization treatment, and (d) eliminating the skull replica.

According to another feature of this process, the production of the skull replica comprises the following steps:

(1) taking an impression of the skull in order to obtain a mold of a first material, said mold having a cavity, (2) pouring a second material into said cavity, (3) allowing the second material to harden so as to obtain a solid mass, and (4) extracting said solid mass constituting the skull replica.

Optionally, the process involves a supplementary step performed after step (a) and before step (b), which consists of placing a thermostable film on the skull replica, said thermostable film being subsequently removed after step (d). It can also be advantageous to provide another stage, which is performed before (step (b) and which consists of depositing a mold release agent prior to the deposition of the first layer.

According to another feature of this process, the polymerization treatment is performed in an autoclave at a temperature of 125° for 24 hours.

The elimination of the skull replica can take place by any known means, e.g. by mechanical means or by dissolving in an appropriate solvent.

It is also possible to provide a supplementary step, performed after step (b) and consisting of making holes, each of which passes through the three layers. Finally, a further stage can be provided after step (d), which consists of machining the protective skull cap when finished, in order to adapt it to the dimensions of the cranium area which it is wished to protect.

BRIEF DESCRIPTION OF THE DRAWINGS

The invention is described in greater detail hereinafter relative to non-limitative embodiments and the attached drawings, wherein show.

DETAILED DESCRIPTION OF THE INVENTION

Figure 1:
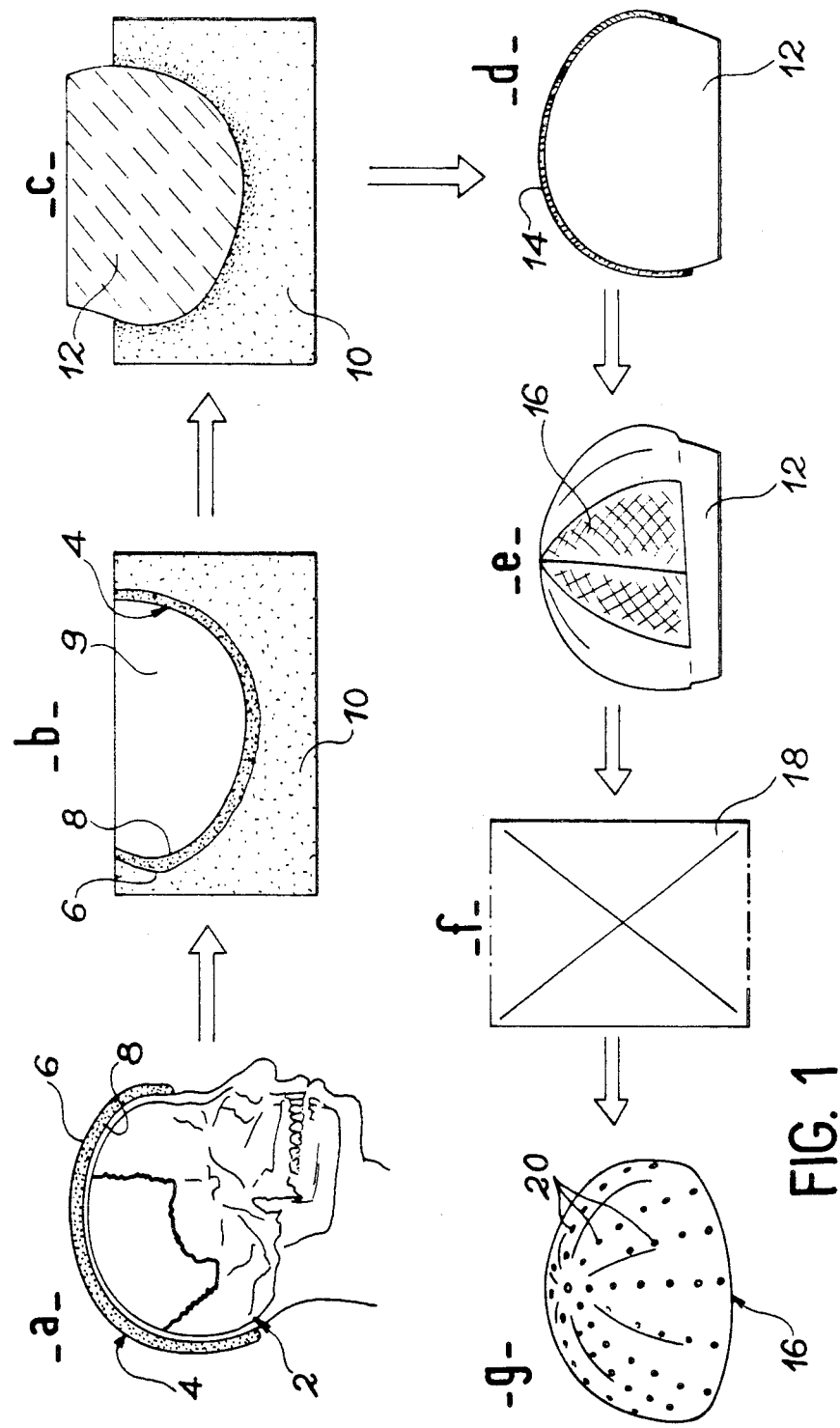
FIGS. 1a to 1g Diagrammatic view illustrating the different step of the process for producing the protective skull cap according to the invention.

The production of such a skull cap is illustrated in FIGS. 1a to 1g. FIGS. 1a show that firstly an impression of the skull 2 is made, using any appropriate material for producing a provisional skull cap 4 having an outer face 6 and an inner face 8. FIG. 1b shows that the provisional skull cap 4 is then placed n a mass 10 of a first material, the outer face 6 of the provisional skull cap 4 being in contact with said material, whilst the inner face 8 is turned upwards, thus defining a cavity 9. For producing the replica of the skull or cranium, into cvity 9 is poured a mass 12 of an appropriate material, e.g. plaster (FIG. 1c) which is allowed to harden or set, so as to obtain a solid mass 12. The latter is then extracted from mold 10 and constitutes a precise replica of the skull 2. FIG. 1d shows that the following operation consists of placing a thermostable film, e.g. a vinyl film 14 on the replica 12 of the skull. The function of this thermostable film will be explained hereinafter. The following stage, illustrated by FIG. 1e, consists of successively positioning the three aforementioned layers which serve to produce the protective skull cap 16. The formation of this skull cap will be described hereinafter relative to FIG. 2. Once the three layers forming skull cap 16 have been deposited, the assembly is placed in an oven 18 (FIG. 1f), where it undergoes a polymerization treatment, which can be an autoclave treatment at 125° C. for 24 hours. Following baking or stoving, the entity is extracted from the oven and the skull replica 12 is eliminated, either by a mechanical operation, or by dissolving in a solvent. This is followed by the removal of the thermostable film and, if desired, a certain number of holes 20 are made in the skull cap 16 (FIG. 1g). The presence of holes 20 permits natural heat exchange for the skin and prevents excessive perspiration.

It should be noted that the protective skull cap 16 undergoes a slight shrinkage due to the polymerization treatment in oven 18. It is in order to take account of this shrinkage that the thermostable film 14 illustrated in FIG. 1d is positioned so that, after shrinkage, the dimensions of protective skull cap 16 exactly correspond to those of the skull.

Figure 2:
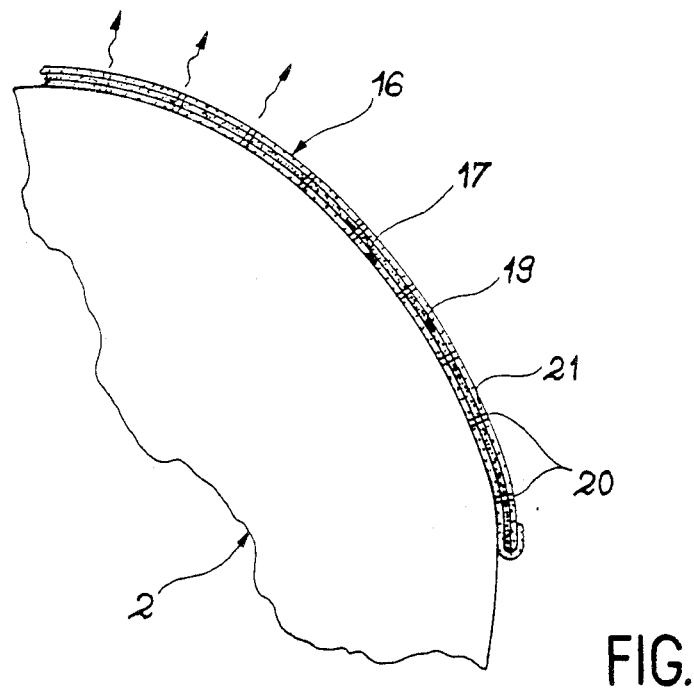
FIG. 2 A diagrammatic sectional view of the structure of such a skull cap placed on the skull.

The structure of the skull cap can best be gathered from FIG. 2, where it can be seen that, from the inside to the outside, it comprises three layers, namely a first carbon fabric layer 17, a second ARAMIDE fiber fabric layer 19 and a third carbon fabric layer 21. Preferably, the three layers are impregnated with a very high elongation resin.

For this purpose, it is possible to use an epoxy resin, into which is incorporated an ester and which has the following characteristics at a temperature of 20° C.

|  | Young modulus (MPa) | Breaking stress (MPa) | Elongation at break (%) |
| --- | --- | --- | --- |
| Traction | 20 | 5.6 | 60 |
| Compression | 85 | 49.0 | 65 |

Such a resin can e.g. be obtained by mixing 42.9% by weight of the GOODRICH product HYCAR CTBN, which is imported into France by POLYPLASTIQUE, 25.9% by weight of the SHELL CHIMIE product EPIKOTE, 30.2% succinic dodecanyl anhydride and 1% tin octoate. This resin, which is liquid prior to polymerization, polymerizes by treating for 24 hours at a temperature of approximately 120° to 125° C. The three layers constituting the skull cap are impregnated whilst the resin is still liquid and then the skull cap is placed in an oven at 120° or 125° C. for 24 hours to polymerize the resin.

For testing purposes, a series of protections of this type were produced, in which layers 17 and 21 were of TORAY T 300 1000 filament carbon fabric and the second layer 19 was of satin KEVLAR ARAMIDE fibre fabric. Each of the three layers was impregnated with the aforementioned very high elongation resin. Carbon gives the rigidity and the strength of the protection. KEVLAR gives a good impact resistance and a high vibration damping power. The high elongation resin is an epoxy resin making it possible to obtain very considerable bending strains, thus limiting risks of the protection deteriorating when the patient puts it on or removes it.

FIG. 2 also shows that the skull cap 16 has a certain number of holes 20 to permit heat exchanges between the skin of the cranium and the ambient air, thereby preventing excessive perspiration.

Figure 3:
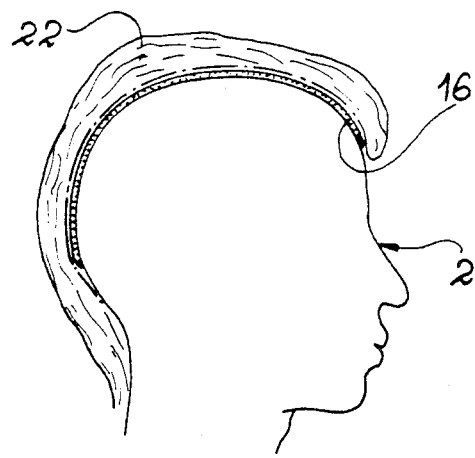
FIG. 3 A diagrammatic view showing how it is possible to position a wig, so as to camouflage the protective skull cap.

The protective skull cap according to the invention has numerous advantages, the most important being that it is light and pleasant to wear. Thus, the skull caps produced have thicknesses varying between 3/10 mm and 5/10 mm and a weight between approximately 30 and 60 g. The skull cap perfectly adapts to the shape of the skull and is worn directly on the skin as a result of its flexibility. As has been shown, the materials from which it is made give very high mechanical performances. Moreover, as can be seen in FIG. 3, a wig 22 can be directly installed on the skull cap 16, which makes the latter completely invisible and removes all complexes from which a person could suffer as a result of having to wear this protection. The shape of the skull cap, together with its great lightness makes it wearable for long periods, particularly as a result of the holes 20 permitting natural heat exchange of the skin and preventing excessive perspiration.

We claim:

1. A protective skull cap for at least partly covering a skull, said cap being worn directly on the skin and being flexible to perfectly adapt to the shape of the skull so as to be in close contact therewith at all points, said skull cap consisting of three layers, from the inside to the outside, a first carbon fabric layer, a second polyarylamide fiber fabric layer and a third carbon fabric layer, the layers being impregnated with a high elongation resin and the thickness of the cap being equal to or less than 1 mm.

2. A protective skull cap according to claim 1, wherein said cap has a plurality of holes, each passing through the three layers.

3. A protective skull cap according to claim 1, wherein the thickness of the cap is equal to or less than 0.5 mm.

4. A protective skull cap according to claim 3, wherein the thickness of the caps is between 0.3 and 0.5 mm.

* * * * *